United States Patent [19]

Yamamoto et al.

[11] Patent Number: 4,727,172

[45] Date of Patent: Feb. 23, 1988

[54] METHOD FOR THE PREPARATION OF AN ORGANOSILOXANE OLIGOMER AND A NOVEL ORGANOSILOXANE OLIGOMER THEREBY

[75] Inventors: Akira Yamamoto; Minoru Takamizawa; Toshinobu Ishihara; Tadao Kurosaki, all of Niigata, Japan

[73] Assignee: Shin-Etsu Chemical Co., Ltd., Tokyo, Japan

[21] Appl. No.: 905,576

[22] Filed: Sep. 9, 1986

[30] Foreign Application Priority Data

Sep. 12, 1985 [JP] Japan .................................. 60-202131
Sep. 17, 1985 [JP] Japan .................................. 60-204781

[51] Int. Cl.$^4$ .............................................. C07F 7/08
[52] U.S. Cl. .................................... 556/440; 556/451; 556/453; 556/454; 556/455; 556/456
[58] Field of Search ............... 556/440, 451, 453, 454, 556/456, 455

[56] References Cited

U.S. PATENT DOCUMENTS 2,961,425 11/1960 Pierce et al. ........................ 556/454
3,006,878 10/1961 Talcott ................................ 556/451
3,377,371 4/1968 Quaal ................................. 556/440

*Primary Examiner*—Paul F. Shaver
*Attorney, Agent, or Firm*—Jules E. Goldberg

[57] ABSTRACT

An efficient method is proposed for the preparation of an organosiloxane oligomer represented by the general formula $YSi(R^1)_n(-O-SiR_3)_{3-n}$, in which each of the groups denoted by R and $R^1$ is a halogen-substituted or unsubstituted monovalent hydrocarbon group having 1 to 8 carbon atoms, Y is a hydrogen atom or a monovalent group selected from methyl, phenyl, vinyl, chloromethyl and 3-(meth)acryloxypropyl groups and n is zero, 1 or 2, by the reaction of an organosilicon halomagnesium salt of the formula $R_3Si-O-MgX$, in which X is a halogen atom, and an organosilane compound of the general formula $YSi(R^1)_n(Z)_{3-n}$, in which Z is a halogen atom or a lower alkoxy group. In particular, tetrasiloxane compounds represented by the general formula $Y^1Si[-O-Si(CH_3)_2(CH_2CH_2CF_3)]_3$, in which $Y^1$ is a hydrogen atom, chloromethyl group or 3-methacryloxypropyl group, are each a novel compound not known in the prior art.

2 Claims, 3 Drawing Figures

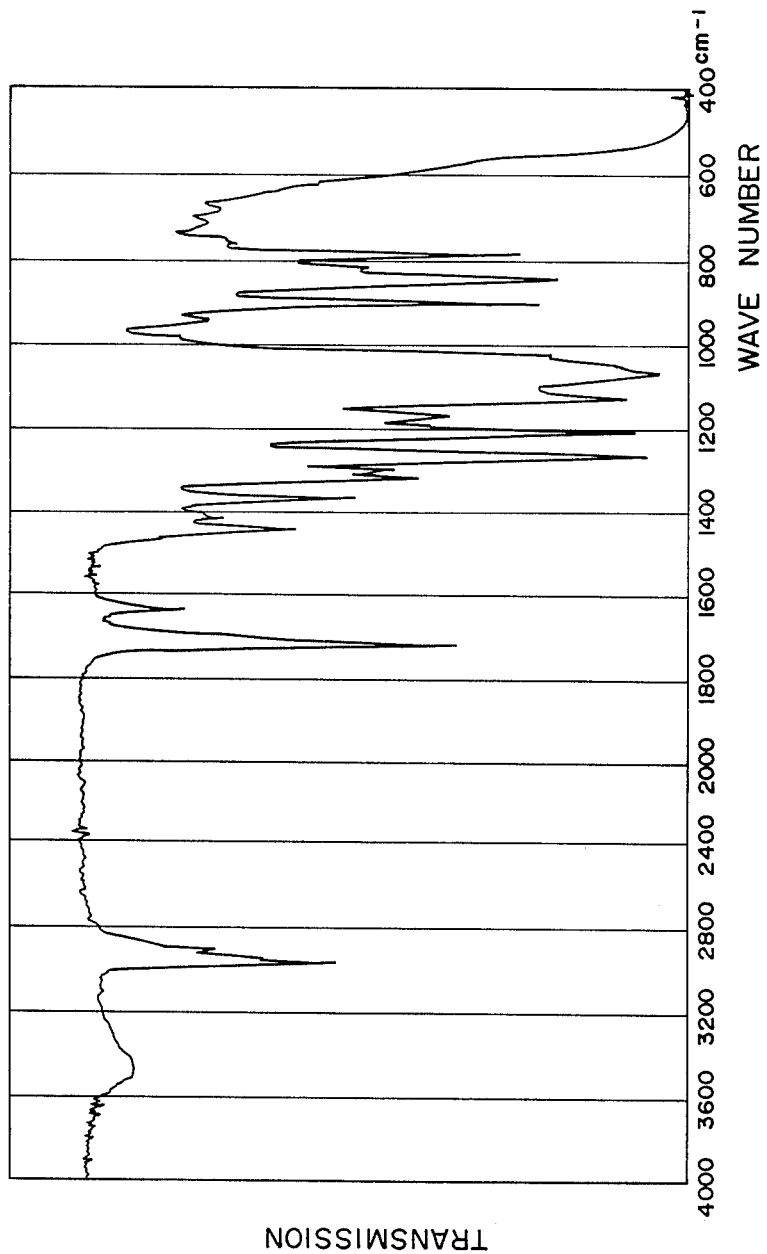

METHOD FOR THE PREPARATION OF AN ORGANOSILOXANE OLIGOMER AND A NOVEL ORGANOSILOXANE OLIGOMER THEREBY

BACKGROUND OF THE INVENTION

The present invention relates to a method for the preparation of an organosiloxane oligomer and a novel organosiloxane oligomer prepared by the method. More particularly, the invention relates to a method for the preparation of an organosiloxane oligomer represented by the general formula $$YSi(R^1)_n(-O-SiR_3)_{3-n},$$

in which each of the groups denoted by R and $R^1$ is, independently from the others, a halogen-substituted or unsubstituted monovalent hydrocarbon group having 1 to 8 carbon atoms, Y is a monovalent atom or group selected from the class consisting of a hydrogen atom, methyl group, phenyl group, vinyl group, chloromethyl group, 3-methacryloxypropyl group and 3-acryloxypropyl group and n is zero, 1 or 2. Among such organosiloxane oligomers, in particular, those expressed by the general formula $$Y^1Si[-O-Si(CH_3)_2(CH_2CH_2CF_3)]_3,$$

in which $Y^1$ is a hydrogen atom, chloromethyl group or 3-methacryloxypropyl group, are novel organosilicon compounds not known in the prior art or not described in any literatures.

As is known, recent progress in the modern high technologies requires supply of various novel materials having high performance and organopolysiloxane or so-called silicone products are also not outside this current. In order to obtain a novel silicone product of high performance, one of the basically important conditions is to develop a variety of intermediate compounds or organosiloxane oligomers such as those represented by the general formula $YSi(R^1)_n(-O-SiR_3)_{3-n}$, in which each symbol has the meaning defined above. The organosiloxane oligomers represented by this general formula of course include those relatively simple organopolysiloxane compounds which can be prepared by a known prior art method without particular problems. When a specific organosiloxane oligomer useful in a specific application is desired, however, no prior art method is known which is generally applicable to the preparation of various kinds of such organo-siloxane oligomers so that it is very important to develop such a method having versatility. In particular, no industrially advantageous method is known for the preparation of an organosiloxane oligomer having an unsymmetrical molecular structure such as 1,1,3,3-tetramethyl-3-vinyl disiloxane, which, in the prior art method, is prepared by the cohydrolysis-cocondensation reaction of dimethyl chlorosilane and dimethyl vinyl chloro-silane only in a low yield.

SUMMARY OF THE INVENTION

Thus, the present invention has an object to provide a method for the preparation of an organosiloxane oligomer represented by the general formula $$YSi(R^1)_n(-O-SiR_3)_{3-n} \qquad (I)$$

in which each of the groups denoted by R and $R^1$ is, independently from the others, a halogen-substituted or unsubstituted monovalent hydrocarbon group having 1 to 8 carbon atoms, Y is a monovalent atom or group selected from the class consisting of a hydrogen atom, methyl group, phenyl group, vinyl group, chloromethyl group, 3-methacryloxypropyl group and 3-acryloxypropyl group and n is zero, 1 or 2, and the inventive method com-prises reacting an organosilicon halomagnesium salt of the general formula $$R_3Si-O-MgX, \qquad (II)$$

in which X is a halogen atom and R has the same meaning as defined above, and an organosilane compound represented by the general formula $$YSi(R^1)_n(Z)_{3-n}, \qquad (III)$$

in which $R^1$, Y and n each have the same meaning as defined above and Z is a halogen atom or a lower alkoxy group.

The present invention also provides a class of novel organosiloxane oligomers represented by the general formula $$Y^1Si[-O-Si(CH_3)_2(CH_2CH_2CF_3)]_3, \qquad (IV)$$

in which $Y^1$ is a hydrogen atom, chloromethyl group or 3-methacryloxypropyl group.

BRIEF DESCRIPTION OF THE DRAWING

FIGS. 1, 2 and 3 are each an infrared absorption spectrum of the organosiloxane oligomer prepared in Example 1, 2 or 3, respectively.

DETAILED DESCRIPTION OF THE PREFERRED EMBODIMENTS

Figure 1:
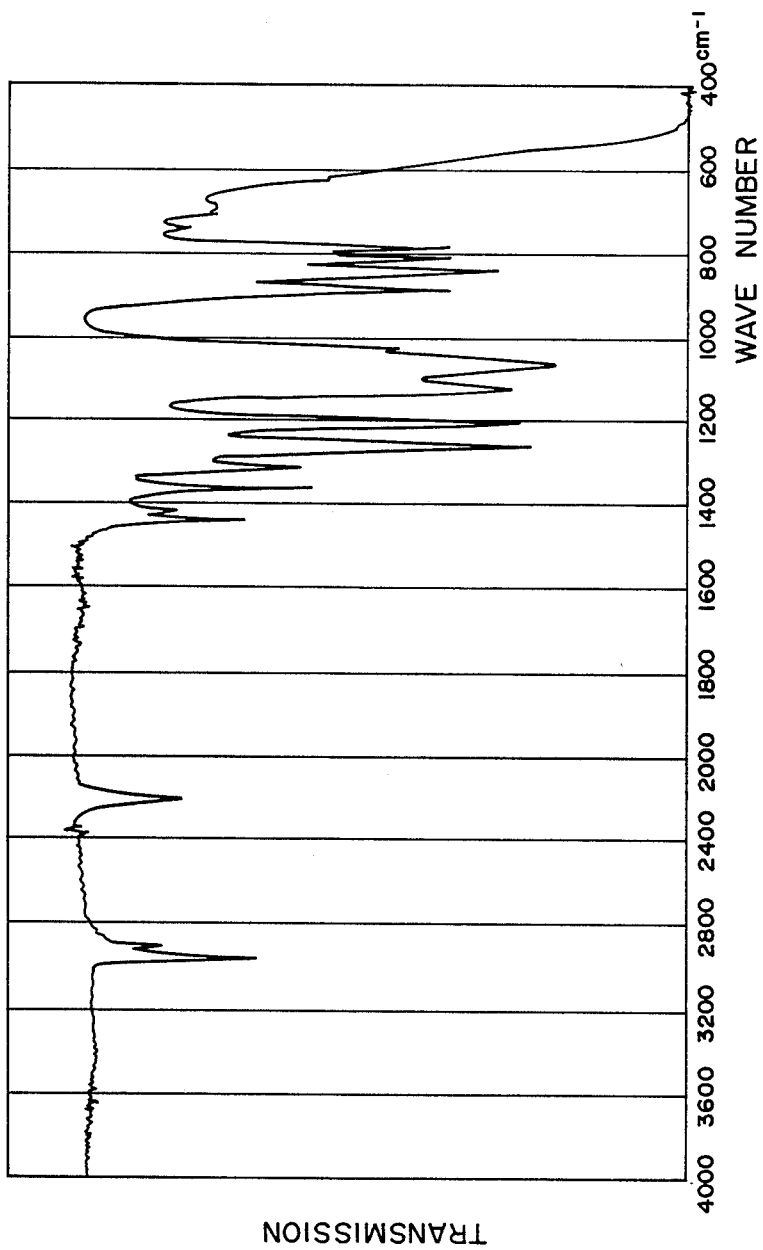

The organosiloxane oligomer as the object of the inventive method is represented by the above given general formula (I). In the formula, each of the groups denoted by the symbols R and $R^1$ is a halogen-substituted or unsubstituted monovalent hydrocarbon group having 1 to 8 carbon atoms exemplified by alkyl groups, e.g. methyl, ethyl, propyl, butyl and octyl groups, cycloalkyl groups, e.g. cyclohexyl and cyclopentyl groups, alkenyl groups, e.g. vinyl and allyl groups, aryl groups, e.g. phenyl, tolyl and xylyl groups, and aralkyl groups, e.g. benzyl and 2-phenylethyl groups, as well as those substituted groups obtained by replacing a part or all of the hydrogen atoms in the above named hydrocarbon groups with halogen, e.g. fluorine and chlorine, atoms exemplified by chloromethyl and 3,3,3-trifluoropropyl groups. The symbol Y in the formula, on the other hand, denotes a hydrogen atom or a monovalent group selected from the class consisting of a methyl group, phenyl groupl, vinyl group, chloromethyl group, 3-methacryloxypropyl group of the formula $CH_2=C(CH_3)-CO-O-(-CH_2-)_3-$ and 3-acryloxypropyl group of the formula $CH_2=CH-CO-O-(-CH_2-)_3-$. The subscript n is a number of zero, 1 or 2 so that the oligomer is a tetra-, tri- or disiloxane, respectively.

Particular examples of the organosiloxane oligomers in conformity with the above given definition include those compounds expressed by the following structural formulas, denoting methyl and vinyl groups with Me and Vi, respectively:

H—SiMe₂—O—SiMe₃;  H—SiMe₂—O—SiMe₂Vi;
H—SiMe₂—O—SiMe₂—CH₂Cl;
H—SiMe₂—O—SiMe₂—CH₂CH₂CF₃;
HSiMe(—O—SiMe₃)₂; HSiMe(—O—SiMe₂Vi)₂;
HSiMe(—OSiMe₂—CH₂Cl)₂; HSiMe(—O—SiMe₂—CH₂CH₂CF₃)₂;
HSi(—O—SiMe₃)₃; HSi(—O—SiMe₂Vi)₃;
HSi(—O—SiMe₂—CH₂Cl)₃;
Vi—SiMe₂—O—SiMe₃; Vi—SiMe₂—O—SiMe₂—O—SiMe₂—CH₂Cl;
Vi—SiMe₂—O—SiMe₂—CH₂CH₂CF₃;
ViSiMe(—O—SiMe₂Vi)₂;
ViSiMe(—O—SiMe₂—CH₂Cl)₂; ViSiMe(—O—SiMe₂—CH₂CH₂CF₃)₂;
ViSi(—O—SiMe₃)₃; ViSi(—O—SiMe₂Vi)₃;
ViSi(—O—SiMe₂—CH₂Cl)₃;
ViSi(—O—SiMe₂—CH₂CH₂CF₃)₃;
ClCH₂—SiMe₂—O—SiMe₃;
ClCH₂SiMe(—O—SiMe₃)₂; ClCH₂Si(—O—SiMe₃)₃;
ClCH₂—SiMe₂—O—SiMe₂—CH₂CH₂CF₃;
CH₂=CMe—CO—O—(—CH₂—)₃—Si(—O—SiMe₃)₃;
CH₂=CMe—CO—O—(—CH₂—)₃—SiMe(—O—SiMe₂Vi)₂;
CH₂=CMe—CO—O—(—CH₂—)₃—Si(—O—SiMe₃)₃;
CH₂=CMe—CO—O—(—CH₂—)₃—SiMe(—O—SiMe(—O—SiMe₂—CH₂CH₂CF₃)₂;
CH₂=CH—CO—O—(—CH₂—)₃—SiMe(—O—SiMe₃)₂;
CH₂=CH—CO—O—(—CH₂—)₃—SiMe(—O—SiMe₂—CH₂CH₂CF₃)₂;
HSi(—O—SiMe₂—CH₂CH₂CF₃)₃;
ClCH₂Si(—O—SiMe₂—CH₂CH₂CF₃)₃; and
CH₂=CMe—CO—O—(—CH₂—)₃—Si(—O—SiMe₂—CH₂CH₂CF₃)₃.

Among the above given organosiloxane oligomers, the compounds expressed by the last given three formulas are each a novel compound not known in the prior art or not described in any literatures.

The organosiloxane oligomer described above can be prepared according to the inventive method by the reaction of the organosilicon halomagnesium salt represented by the general formula (II) and the organosilane compound represented by the general formula (III) given above. The reaction proceeds according to the reaction equation:

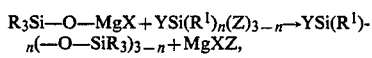

in which each symbol has the same meaning as defined before. The reaction is performed at a temperature in the range from 0° C. to the refluxing temperature of the reaction mixture or, preferably, in the range from 30° to 80° C. After completion of the reaction, the reaction mixture is poured into a large volume of water to remove the magnesium salt and the organic layer separated from the aqueous phase is distilled to give the desired organosiloxane oligomer in a high purity and in a high yield.

The organosilicon halomagnesium salt represented by the general formula (II) can be prepared by the dropwise addition of an organopolysiloxane of a cyclic or linear molecular structure represented by the general formula, (—SiR₂—O—)ₘ, in which m is a positive intgeger, into a solution of a Grignard reagent of the formula RMgX to react them at a temperature in the range from 50° to 120° C. Particular examples of the organosilicon halomagnesium salts suitable for the reaction include those compounds expressed by the following formulas, in which Me, Ph and Vi denote methyl, phenyl and vinyl groups, respectively: Me₃Si—O—MgCl; Me₂PhSi—O—MgBr; Me₂ViSi—O—MgCl; (ClCH₂)Me₂Si—O—MgCl; and (CF₃CH₂CH₂)Me₂Si—O—MgCl.

On the other hand, particular examples of the organosilane compounds represented by the general formula (III) to be reacted with the organosilicon halomagnesium salt include methyl dichlorosilane, dimethyl chlorosilane, methyl diethoxy silane, trimethoxy silane, vinyl methyl dichlorosilane, vinyl dimethyl chlorosilane, vinyl trichlorosilane, phenyl trichlorosilane, chloromethyl methyl dichlorosilane, chloromethyl dimethyl chlorosilane, chloromethyl trichlorosilane, 3-methacryloxypropyl trichlorosilane, 3-methacryloxypropyl methyl dichlorosilane, methyl trichlorosilane, trimethyl chlorosilane and the like.

In the following, the method of the invention and characterization of the novel organosiloxane oligomers prepared by the method are described in more detail by way of examples.

EXAMPLE 1

Into a reaction vessel were introduced 24.3 g (1 mole) of metallic magnesium and 300 ml of tetrahydrofuran and gaseous methyl chloride was blown into the reaction mixture in the reaction vessel to prepare a tetrahydrofuran solution of methyl magnesium chloride. Thereafter, a solution prepared by dissolving 156 g of 1,3,5-tris(3,3,3-trifluoropropyl)-1,3,5-trimethyl cyclotrisiloxane in 200 ml of tetrahydrofuran was added dropwise into the mixture in the reaction vessel over a period of 2 hours and the reaction mixture was heated for additional 2 hours under reflux. Further, 45 g (0.33 mole) of trichlorosilane were added dropwise into the reaction mixture under continued refluxing. The reaction mixture was then poured into 1 liter of water and the organic solution separated from the aqueous phase was distilled under reduced pressure to give 146 g of a fraction boiling at 125° C. under a pressure of 4 mmHg. This fraction had a purity of 99.2% according to the gas chromatographic analysis and a refractive index $n_D^{25}$ of 1.3700. The infrared absorption spectrum shown in FIG. 1 and the results of the NMR and elementary analyses shown below supported that the thus obtained product was an organosiloxane oligomer tris(3,3,3-trifluoropropyl dimethyl siloxy)silane of the formula HSi(—O—SiMe₂—CH₂CH₂CF₃)₃.

| Results of NMR analysis | | |
|---|---|---|
| δ0.17 ppm | —SiCH₃ | 18H |
| δ0.77 ppm | —SiCH₃ | 6H |
| δ2.0 ppm | —CH2CF₃ | 6H |
| δ5.25 ppm | —SiH | 1H |
| Results of elementary analysis | | |
| | C, % | H, % | Si, % |
| Calculated as C₁₅H₃₁O₃F₉Si₄ | 33.19 | 5.76 | 20.70 |
| Found | 33.16 | 5.76 | 20.74 |

EXAMPLE 2

Figure 2:
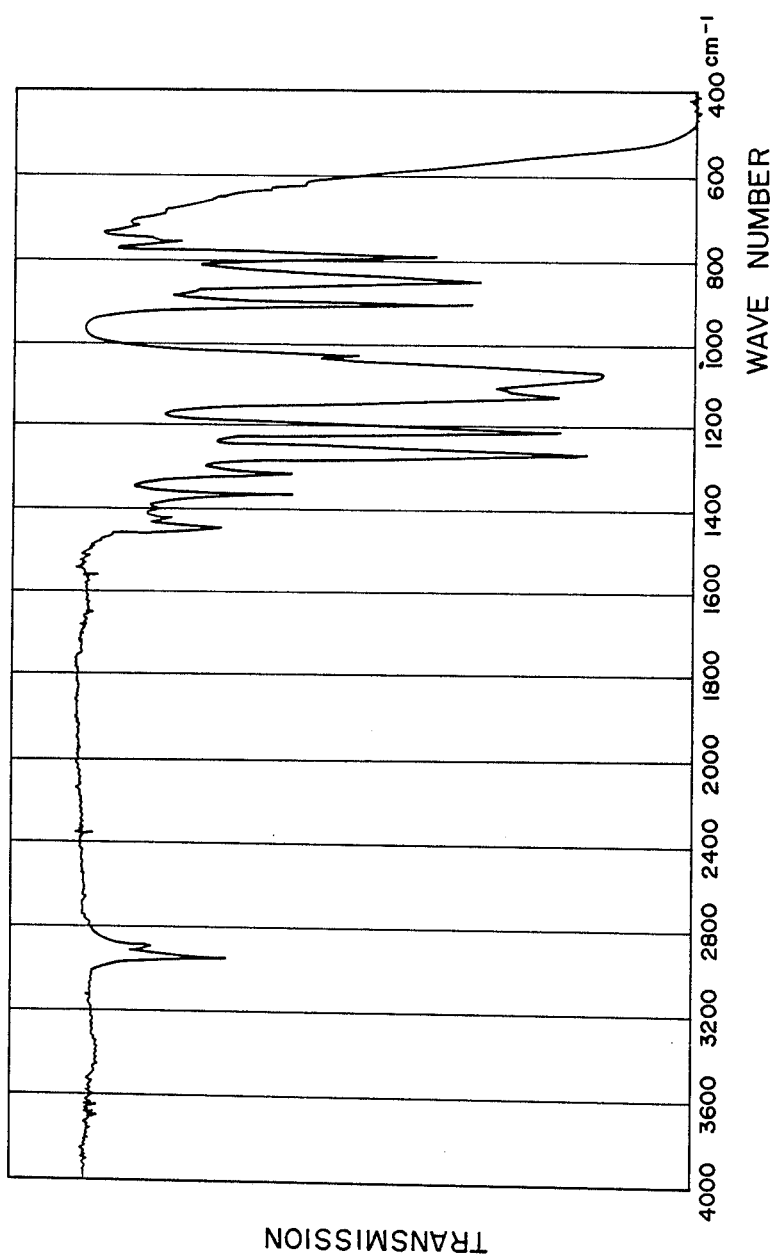

The experimental procedure was substantially the same as in Example 1 except that 45 g of trichlorosilane used in Example 1 were replaced with 61 g of chloromethyl trichlorosilane to give 156 g of a fraction boiling at 139° C. under a pressure of 4 mmHg and having a refractive index $n_D^{25}$ of 1.3850 as a product. The purity of the product was 96% according to the gas chromatographic analysis. The infrared absorption spectrum shown in FIG. 2 and the results of the NMR and elementary analyses shown below supported that the thus obtained product was an organosiloxane oligomer chloromethyl tris(3,3,3-trifluoropropyl dimethyl siloxy)silane of the formula ClCH$_2$Si(—O—SiMe$_2$—CH$_2$CH$_2$CF$_3$)$_3$.

| Results of NMR analysis | | |
|---|---|---|
| δ0.17 ppm | —SiCH$_3$ | 18H |
| δ0.77 ppm | —SiCH$_3$ | 6H |
| δ2.0 ppm | —CH$_2$CF$_3$ | 6H |
| δ2.55 ppm | —SiCH$_2$Cl | 2H |
| Results of elementary analysis | | |
| | C, % | H, % | Si, % |
| Calculated as C$_{16}$H$_{32}$O$_3$ClF$_9$Si$_4$ | 32.56 | 5.46 | 19.00 |
| Found | 32.59 | 5.47 | 18.96 |

EXAMPLE 3

The experimental procedure was substantially the same as in Example 1 except that 45 g of trichlorosilane used in Example 1 were replaced with 86 g of 3-methacryloxypropyl trichlorosilane to give 161 g of a fraction boiling at 156° C. under a pressure of 1 mmHg and having a refracstive index $n_D^{25}$ of 1.4005. The purity of the product was 96% according to the gas chromatographic analysis. The infrared absorption spectrum shown in FIG. 3 and the results of the NMR and elementary analyses shown below supported that this product was an organosiloxane oligomer 3-methacryloxypropyl tris(3,3,3-trifluoropropyl dimethyl siloxy)silane of the formula CH$_2$=CMe—CO—O—(—CH$_2$—)$_3$—Si(—O—SiMe$_2$—CH$_2$CH$_2$CF$_3$)$_3$.

EXAMPLE 4

Hydrolysis of methyl vinyl dichlorosilane was performed by adding 141 g (1 mole) of the silane into 500 ml of water under agitation and the organopolysiloxane mixture separated from the aqueous phase was dehydrated over anhydrous calcium chloride. The thus obtained mixture of cyclic vinyl methyl siloxane oligomers was added dropwise into a tetrahydrofuran solution of 1 mole of methyl magnesium chloride prepared in the same manner as in Example 1 and kept at 66° and 70° C. and the reaction was completed by heating the reaction mixture under reflux for additional two hours after completion of the dropwise addition of the organosiloxane mixture to give a chloromagnesium salt of dimethyl vinyl silanol. In the next place, 143 g (1 mole) of chloromethyl dimethyl chlorosilane were added dropwise into the reaction mixture ketp at 40° C. to effect the reaction with the chloromagnesium salt. The reaction mixture was poured into 1 liter of water to remove the salt and the organic phase separated from the aqueous phase was distilled under reduced pressure to give 158 g of a fraction boiling at 68° C. under a pressure of 14 mmHg. This fraction had a purity of 99% by the gas chromatographic analysis and was identified to be 1-chloromethyl-3-vinyl-1,1,3,3-tetramethyl disiloxane.

EXAMPLE 5

Into a reaction vessel were introduced 234.3 g (1 mole) of metallic magnesium and 300 ml of tetrahydrofuran and then 157 g (1 mole) of bromobenzene were added to the mixture in the reaction vessel to prepare a tetrahydrofuran solution of phenylmagnesium bromide into which 74 g of octamethyl cyclotetrasiloxane were added over a period of 4 hours under reflux. After completion of the dropwise addition of the cyclotetrasiloxane, the reaction mixture was further heated under reflux for additional two hours to complete the reaction for the formation of bromomagnesium salt of phenyl dimethyl silanol. In the next place, 90 g of dimethyl methoxy silane were added droplwise to the reaction mixture kept at 40° C. and the reaction mixture was heated for additional one hour under reflux followed by cooling to room temperature. The reaction mixture was poured into 1 liter of 5% hydrochloric acid and the organic phase separated from the aqueous phase was distilled under reduced pressure to give 149 g of a fraction boiling at 92° C. under a pressure of 15 mmHg. This fraction had a purity of 98% by the gas chromatographic analysis and was identified to be 1-phenyl-1,1,3,3-tetramethyl disiloxane.

What is claimed is:

1. A method for the preparation of an organosiloxane oligomer represented by the general formula

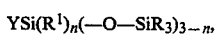

YSi(R$^1$)$_n$(—O—SiR$_3$)$_{3-n}$, in which each of the groups denoted by R and R$^1$ is, independently from the others, a halogen-substituted or unsubstituted monovalent hydrocarbon group having 1 to 8 carbon atoms, Y is a hydrogen atom or a monovalent group selected from the class consisting of methyl, phenyl, vinyl, chloromethyl, 3-methacryloxypropyl and 3-acryloxypropyl groups and n is zero, 1 or 2, which comprises reacting an organosilicon halomagnesium salt of the general formula

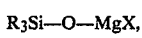

R$_3$Si—O—MgX, in which R has the same meaning as defined above and X is a halogen atom, and an organosilane compound represented by the general formula

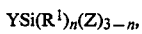

YSi(R$^1$)$_n$(Z)$_{3-n}$, in which R$^1$, Y and n each have the same meaning as defined above and Z is a halogen atom or a lower alkoxy group.

2. A method for the preparation of an organosiloxane oligomer represented by the general formula

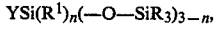

YSi(R$^1$)$_n$(—O—SiR$_3$)$_{3-n}$, in which each of the groups denoted by R and R$^1$ is, independently from the others, a halogen-substituted or unsubstituted monovalent hydrocarbon group having 1 to 8 carbon atoms, Y is a hydrogen atom or a monovalent group selected from the class consisting of methyl, phenyl, vinyl, chloromethyl, 3-methacryloxypropyl and 3-acryloxypropyl groups and n is zero, 1 or 2, which comprises reacting a cyclic or linear organopolysiloxane represented by the general formula —(—SiR$_2$—O—)$_m$— with a Grignard reagent represented by the general formula RMgX, in which R has the same meaning as defined above and X is a halogen atom, to form an organosilicon halomagnesium salt of the general formula R$_3$Si—O—MgX and reacting the organosilicon halomagnesium salt with an organosilane compound represented by the general formula YSi(R$_1$)$_n$(Z)$_{3-n}$, in which R$_1$ and Y each have the same meaning as defined above and Z is a halogen atom or a lower alkyl group.

* * * * *